US009095326B2

(12) United States Patent
Ritchie et al.

(10) Patent No.: US 9,095,326 B2
(45) Date of Patent: Aug. 4, 2015

(54) BIOPSY SYSTEM WITH VACUUM CONTROL MODULE

(75) Inventors: Paul G. Ritchie, Loveland, OH (US); Trevor W. V. Speeg, Williamsburg, OH (US); Wells D. Haberstich, Loveland, OH (US); John A. Hibner, Mason, OH (US)

(73) Assignee: DEVICOR MEDICAL PRODUCTS, INC., Cincinnati, OH (US)

( * ) Notice: Subject to any disclaimer, the term of this patent is extended or adjusted under 35 U.S.C. 154(b) by 988 days.

(21) Appl. No.: 11/952,393

(22) Filed: Dec. 7, 2007

(65) Prior Publication Data

US 2008/0146962 A1    Jun. 19, 2008

Related U.S. Application Data

(60) Provisional application No. 60/869,736, filed on Dec. 13, 2006, provisional application No. 60/874,792, filed on Dec. 13, 2006.

(51) Int. Cl.
*A61B 10/02* (2006.01)

(52) U.S. Cl.
CPC ......... *A61B 10/0275* (2013.01); *A61B 10/0283* (2013.01); *A61B 2010/0225* (2013.01)

(58) Field of Classification Search
CPC ........... A61B 10/0233; A61B 10/0266; A61B 10/0275; A61B 10/0283
USPC .......... 600/562, 565, 566; 604/317, 319, 320, 604/321, 322
See application file for complete search history.

(56) References Cited

U.S. PATENT DOCUMENTS

| 2,853,071 | A | 9/1958 | Saffir |
| 3,630,192 | A | 12/1971 | Jamshidi |
| 3,719,086 | A | 3/1973 | Bannister et al. |
| 3,994,297 | A | 11/1976 | Kopf |

(Continued)

FOREIGN PATENT DOCUMENTS

| EP | 0 890 339 | 1/1999 |
| EP | 0995400 A | 4/2000 |

(Continued)

OTHER PUBLICATIONS

EnCor MRI Specifications and Breast Biopsy System, SenoRx, 2005, pp. 102.

(Continued)

*Primary Examiner* — Sean Dougherty
*Assistant Examiner* — Michael C Stout
(74) *Attorney, Agent, or Firm* — Frost Brown Todd LLC

(57) ABSTRACT

A biopsy system includes a biopsy device having a translating cutter for severing tissue samples and a vacuum control module. The vacuum control module is separate from the biopsy device. The vacuum control module includes a vacuum pump and vacuum canister, and is portable by a single hand. The vacuum canister and the vacuum control module have complimentary ports that are configured to couple upon insertion of the vacuum canister into the vacuum control module. The complimentary ports provide fluid communication between a vacuum pump in the vacuum control module and a reservoir in the vacuum canister. The biopsy device may be placed in fluid communication with the vacuum pump via the canister without the user having to separately connect any tubes with the canister or pump.

7 Claims, 9 Drawing Sheets

(56) References Cited

U.S. PATENT DOCUMENTS

| | | | |
|---|---|---|---|
| 4,013,076 A * | 3/1977 | Puderbaugh et al. | 604/320 |
| 4,051,852 A | 10/1977 | Villari | |
| 4,600,014 A | 7/1986 | Beraha | |
| 4,782,833 A | 11/1988 | Einhorn | |
| 5,234,000 A | 8/1993 | Hakky et al. | |
| 5,406,959 A | 4/1995 | Mann | |
| 5,429,596 A * | 7/1995 | Arias et al. | 604/21 |
| 5,439,457 A | 8/1995 | Yoon | |
| 5,466,229 A * | 11/1995 | Elson et al. | 604/317 |
| 5,526,822 A | 6/1996 | Burbank et al. | |
| 5,532,168 A | 7/1996 | Marantz | |
| 5,601,585 A | 2/1997 | Banik et al. | |
| 5,645,209 A | 7/1997 | Green et al. | |
| 5,769,086 A | 6/1998 | Ritchart et al. | |
| 5,769,547 A | 6/1998 | Igarashi | |
| 5,775,333 A | 7/1998 | Burbank et al. | |
| 5,873,967 A | 2/1999 | Clark et al. | |
| 5,876,329 A | 3/1999 | Harhen | |
| 5,919,146 A * | 7/1999 | Propp | 600/577 |
| 5,928,164 A | 7/1999 | Burbank et al. | |
| 5,964,716 A | 10/1999 | Gregoire et al. | |
| 5,980,469 A | 11/1999 | Burbank et al. | |
| 6,007,497 A * | 12/1999 | Huitema | 600/567 |
| 6,017,316 A | 1/2000 | Ritchart et al. | |
| 6,042,593 A | 3/2000 | Storz et al. | |
| 6,077,230 A | 6/2000 | Gregoire et al. | |
| 6,083,177 A | 7/2000 | Kobren et al. | |
| 6,086,544 A | 7/2000 | Hibner et al. | |
| 6,120,462 A | 9/2000 | Hibner et al. | |
| 6,142,946 A | 11/2000 | Hwang et al. | |
| 6,162,187 A | 12/2000 | Buzzard et al. | |
| 6,213,957 B1 | 4/2001 | Milliman et al. | |
| 6,228,055 B1 | 5/2001 | Foerster et al. | |
| 6,231,522 B1 | 5/2001 | Voegele et al. | |
| 6,273,862 B1 * | 8/2001 | Privitera et al. | 600/568 |
| 6,402,701 B1 | 6/2002 | Kaplan et al. | |
| 6,409,970 B1 | 6/2002 | Phifer | |
| 6,419,654 B1 * | 7/2002 | Kadan | 604/27 |
| 6,428,486 B2 | 8/2002 | Ritchart et al. | |
| 6,428,487 B1 | 8/2002 | Burdorff et al. | |
| 6,428,510 B1 * | 8/2002 | Kadan | 604/164.04 |
| 6,436,054 B1 | 8/2002 | Viola et al. | |
| 6,485,436 B1 | 11/2002 | Truckai et al. | |
| 6,488,636 B2 | 12/2002 | Bryan et al. | |
| 6,527,731 B2 | 3/2003 | Weiss et al. | |
| 6,544,194 B1 | 4/2003 | Kortenbach | |
| 6,592,530 B1 * | 7/2003 | Farhadi | 600/564 |
| 6,620,111 B2 | 9/2003 | Stephens et al. | |
| 6,626,849 B2 | 9/2003 | Huitema et al. | |
| 6,659,338 B1 | 12/2003 | Dittmann et al. | |
| 6,758,824 B1 | 7/2004 | Miller | |
| 6,849,080 B2 | 2/2005 | Lee et al. | |
| 6,986,748 B2 | 1/2006 | McAlister et al. | |
| 7,025,098 B2 | 4/2006 | Osborne | |
| 7,025,732 B2 | 4/2006 | Thompson et al. | |
| 7,160,273 B2 * | 1/2007 | Greter et al. | 604/319 |
| 7,185,681 B2 | 3/2007 | Romano | |
| 7,189,206 B2 | 3/2007 | Quick et al. | |
| 7,204,811 B2 | 4/2007 | Kortenbach et al. | |
| 7,252,641 B2 | 8/2007 | Thompson et al. | |
| 2,785,991 A1 | 10/2007 | Morris et al. | |
| 7,276,032 B2 | 10/2007 | Hibner | |
| 7,284,965 B2 | 10/2007 | Adahan | |
| 7,442,171 B2 | 10/2008 | Stephens et al. | |
| 7,445,739 B2 | 11/2008 | Tsonton et al. | |
| 7,470,237 B2 | 12/2008 | Beckman et al. | |
| 7,556,622 B2 | 7/2009 | Mark et al. | |
| 7,575,556 B2 | 8/2009 | Speeg et al. | |
| 7,740,594 B2 | 6/2010 | Hibner | |
| 7,740,596 B2 | 6/2010 | Hibner | |
| 7,740,597 B2 | 6/2010 | Cicenas et al. | |
| 7,753,857 B2 | 7/2010 | Hibner | |
| 7,758,515 B2 | 7/2010 | Hibner | |
| 7,806,834 B2 | 10/2010 | Beckman et al. | |
| 7,819,819 B2 | 10/2010 | Quick et al. | |
| 7,828,745 B2 | 11/2010 | McAlister et al. | |
| 7,828,748 B2 | 11/2010 | Hibner | |
| 7,846,107 B2 | 12/2010 | Hoffman et al. | |
| 7,854,706 B2 | 12/2010 | Hibner | |
| 7,854,707 B2 | 12/2010 | Hibner et al. | |
| 7,896,817 B2 | 3/2011 | Garrison | |
| 7,914,464 B2 | 3/2011 | Burdorff et al. | |
| 7,985,239 B2 | 7/2011 | Suzuki | |
| 8,002,713 B2 | 8/2011 | Heske et al. | |
| 8,016,772 B2 | 9/2011 | Heske et al. | |
| 8,016,844 B2 | 9/2011 | Privitera et al. | |
| 8,038,627 B2 | 10/2011 | Hibner | |
| 8,083,687 B2 | 12/2011 | Parihar | |
| 8,118,755 B2 | 2/2012 | Hibner et al. | |
| 8,177,728 B2 | 5/2012 | Hibner et al. | |
| 8,177,729 B2 | 5/2012 | Hibner et al. | |
| 8,206,316 B2 | 6/2012 | Hibner et al. | |
| 8,235,913 B2 | 8/2012 | Hibner et al. | |
| 8,241,226 B2 | 8/2012 | Hibner et al. | |
| 8,251,916 B2 | 8/2012 | Speeg et al. | |
| 8,262,586 B2 | 9/2012 | Almazan et al. | |
| 8,357,103 B2 * | 1/2013 | Mark et al. | 600/566 |
| 8,485,987 B2 | 7/2013 | Videbaek et al. | |
| 8,622,927 B2 | 1/2014 | Parihar et al. | |
| 8,702,623 B2 | 4/2014 | Parihar et al. | |
| 8,911,381 B2 | 12/2014 | Hibner et al. | |
| 2002/0082519 A1 * | 6/2002 | Miller et al. | 600/566 |
| 2002/0120212 A1 | 8/2002 | Ritchart et al. | |
| 2003/0125639 A1 | 7/2003 | Fisher et al. | |
| 2003/0149360 A1 * | 8/2003 | Tardy et al. | 600/437 |
| 2003/0199753 A1 | 10/2003 | Hibner | |
| 2003/0199787 A1 | 10/2003 | Schwindt | |
| 2004/0019299 A1 * | 1/2004 | Ritchart et al. | 600/567 |
| 2004/0054299 A1 * | 3/2004 | Burdorff et al. | 600/564 |
| 2004/0073151 A1 | 4/2004 | Weston | 602/41 |
| 2004/0082915 A1 * | 4/2004 | Kadan | 604/164.04 |
| 2004/0138687 A1 * | 7/2004 | Himes | 606/167 |
| 2004/0210161 A1 * | 10/2004 | Burdorff et al. | 600/566 |
| 2004/0225208 A1 * | 11/2004 | Johnson | 600/364 |
| 2005/0049521 A1 | 3/2005 | Miller et al. | |
| 2005/0065453 A1 * | 3/2005 | Shabaz et al. | 600/564 |
| 2005/0082518 A1 | 4/2005 | Kunitz | |
| 2005/0159677 A1 * | 7/2005 | Shabaz et al. | 600/567 |
| 2005/0215921 A1 * | 9/2005 | Hibner et al. | 600/566 |
| 2005/0215922 A1 | 9/2005 | Tsonton et al. | |
| 2005/0261581 A1 * | 11/2005 | Hughes et al. | 600/434 |
| 2006/0041230 A1 | 2/2006 | Davis | |
| 2006/0074344 A1 | 4/2006 | Hibner | |
| 2006/0074345 A1 * | 4/2006 | Hibner | 600/566 |
| 2006/0149162 A1 * | 7/2006 | Daw et al. | 600/564 |
| 2007/0027407 A1 * | 2/2007 | Miller | 600/566 |
| 2007/0032741 A1 * | 2/2007 | Hibner et al. | 600/566 |
| 2007/0032742 A1 * | 2/2007 | Monson et al. | 600/566 |
| 2007/0038146 A1 * | 2/2007 | Quick et al. | 600/566 |
| 2007/0055173 A1 * | 3/2007 | DeLonzor et al. | 600/564 |
| 2007/0112751 A1 | 5/2007 | Pyun | |
| 2007/0156125 A1 * | 7/2007 | DeLonzor | 606/21 |
| 2007/0179401 A1 * | 8/2007 | Hibner | 600/567 |
| 2008/0004545 A1 | 1/2008 | Garrison | |
| 2008/0082021 A1 | 4/2008 | Ichikawa et al. | |
| 2008/0214955 A1 | 9/2008 | Speeg et al. | |
| 2009/0137928 A1 * | 5/2009 | Quick et al. | 600/566 |
| 2010/0075664 A1 | 3/2010 | Maucksch | |
| 2010/0152610 A1 | 6/2010 | Parihar et al. | |
| 2010/0160819 A1 | 6/2010 | Parihar et al. | |

FOREIGN PATENT DOCUMENTS

| | | |
|---|---|---|
| EP | 1 520 518 | 4/2005 |
| EP | 1 642 533 | 4/2006 |
| EP | 1 642 534 | 4/2006 |
| EP | 1 832 234 | 12/2007 |
| EP | 1 932 481 | 6/2008 |
| EP | 1 932 482 | 6/2008 |
| GB | 2 018 601 | 10/1979 |
| RU | 2021770 | 10/1994 |
| WO | WO 02/036017 | 5/2002 |
| WO | WO 03/077768 | 9/2003 |
| WO | WO 2004/016177 | 2/2004 |

(56) References Cited

FOREIGN PATENT DOCUMENTS

| WO | WO 2004/052179 | 6/2004 |
| --- | --- | --- |
| WO | WO 2004/052212 | 6/2004 |
| WO | WO 2004/075728 | 9/2004 |
| WO | WO 2004075715 A2 * | 9/2004 |
| WO | WO 2006/005342 | 1/2006 |
| WO | WO 2006/124489 | 11/2006 |
| WO | WO 2007/019152 | 2/2007 |
| WO | WO 2007/021904 | 2/2007 |
| WO | WO 2007/112751 | 10/2007 |

OTHER PUBLICATIONS

Australian Office Action dated Apr. 24, 2012 for Application No. AU2007242953.
Australian Office Action dated Nov. 13, 2012 for Application No. AU2007242953.
Chinese Office Action dated Jan. 31, 2012 for Application No. CN201010617451.1.
Chinese Office Action dated Oct. 31, 2012 for Application No. CN201010617451.1.
Chinese Office Action dated Apr. 25, 2013 for Application No. CN201010617451.1.
Chinese Office Action dated Nov. 12, 2013 for Application No. CN201010617451.1.
European Search Report dated Dec. 1, 2005 for Application No. EP 05256035.
European Communication dated Jun. 25, 2007 for Application No. EP 05256035.
European Search Report dated Jun. 13, 2007 for Application No. EP 07250402.
European Search Report dated Nov. 14, 2007 for Application No. EP 07250926.
European Search Report and Written Opinion dated Dec. 11, 2007 for Application No. EP 07253220.
European Search Report dated Mar. 20, 2008 for Application No. EP 07254806.
European Examination Report dated May 13, 2008 for Application No. EP 07250402.
European Examination Report dated Mar. 19, 2009 for Application No. 07250926.
European Search Report and Written Opinion dated Mar. 20, 2009 for Application No. 08252524.
European Search Report and Written Opinion dated Mar. 25, 2009 for Application No. 08252518.
European Search Report and Written Opinion dated Sep. 20, 2010 for Application No. EP 10251076.
European Search Report and Written Opinion dated Apr. 5, 2012 for Application No. EP 11193357.
Supplemental European Search Report dated Dec. 16, 2009 for Application No. EP06789155.
International Preliminary Report on Patentability and Written Opinion dated Feb. 5, 2008 for Application No. PCT/US2006/030022.
International Search Report dated Jul. 18, 2007 for Application No. PCT/US2006/30022.
International Search Report dated Sep. 27, 2007 for Application No. PCT/US2006/30022.
International Search Report dated Dec. 18, 2008 for Application No. PCT/US2008/058627.
U.S. Appl. No. 60/869,736, filed Dec. 13, 2006.
U.S. Appl. No. 60/874,792, filed Dec. 13, 2006.

* cited by examiner

FIG. 8

| Action | "Sample" Button (170) | "Clear Probe" Button (172) | "Aspirate/Insert" Button (174) | Aperture (114) | Lateral Lumen (108) | Master Control Valve (4060) Position | Saline/Vacuum Valve (4080) Position |
|---|---|---|---|---|---|---|---|
| Ready State | — | — | — | closed | sealed/dead-headed | up | up |
| Sample | press & release or press & hold | — | — | open | vacuum | down | down |
| Clear Probe | — | press & release or press & hold | — | closed | vent | middle | up |
| Insert Pain or Bleeding Medication or Apply Marker, etc. | — | — | press & release | closed | saline | down | up |
| | | | | open | vent | middle | down |
| Aspirate Cavity | — | — | press & hold | open | vacuum | down | down |

BIOPSY SYSTEM WITH VACUUM CONTROL MODULE

PRIORITY

This application claims priority to and incorporates by reference U.S. provisional application Ser. No. 60/869,736, filed Dec. 13, 2006, and U.S. provisional application Ser. No. 60/874,792, filed Dec. 13, 2006.

BACKGROUND

Some embodiments of the present invention relate in general to biopsy devices for obtaining tissue samples from within the body, and more particularly to a biopsy system including a lightweight, portable biopsy control module.

When a suspicious tissue mass is discovered in a patient's breast or another area through examination, ultrasound, MRI, X-ray imaging or the like, it may be necessary to perform a biopsy procedure to remove one or more samples of that tissue in order to determine whether the mass contains cancerous cells. A biopsy may be performed using an open or percutaneous method. Medical devices for obtaining tissue samples for subsequent sampling and/or testing are known in the biopsy art. For instance, a biopsy instrument now marketed under the tradename MAMMOTOME is commercially available from Ethicon Endo-Surgery, Inc. for use in obtaining breast biopsy samples. This device generally retrieves multiple core biopsy samples from one insertion into breast tissue with vacuum assistance.

The following patent documents disclose various biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al.

Some vacuum-assisted biopsy devices may employ a reusable control module that includes a vacuum pump and other control apparatus. Such vacuum control modules may be relatively large and heavy, and may be mounted on wheels or on a wheeled platform so that they can be moved from room to room in a surgical area.

While a variety of biopsy systems have been made and used, it is believed that no one prior to the inventors has made or used a biopsy system as described in the appended claims.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

FIG. 8 illustrates multiple control states that can be employed in controlling a biopsy device in a biopsy system.

DETAILED DESCRIPTION

Figure 1:
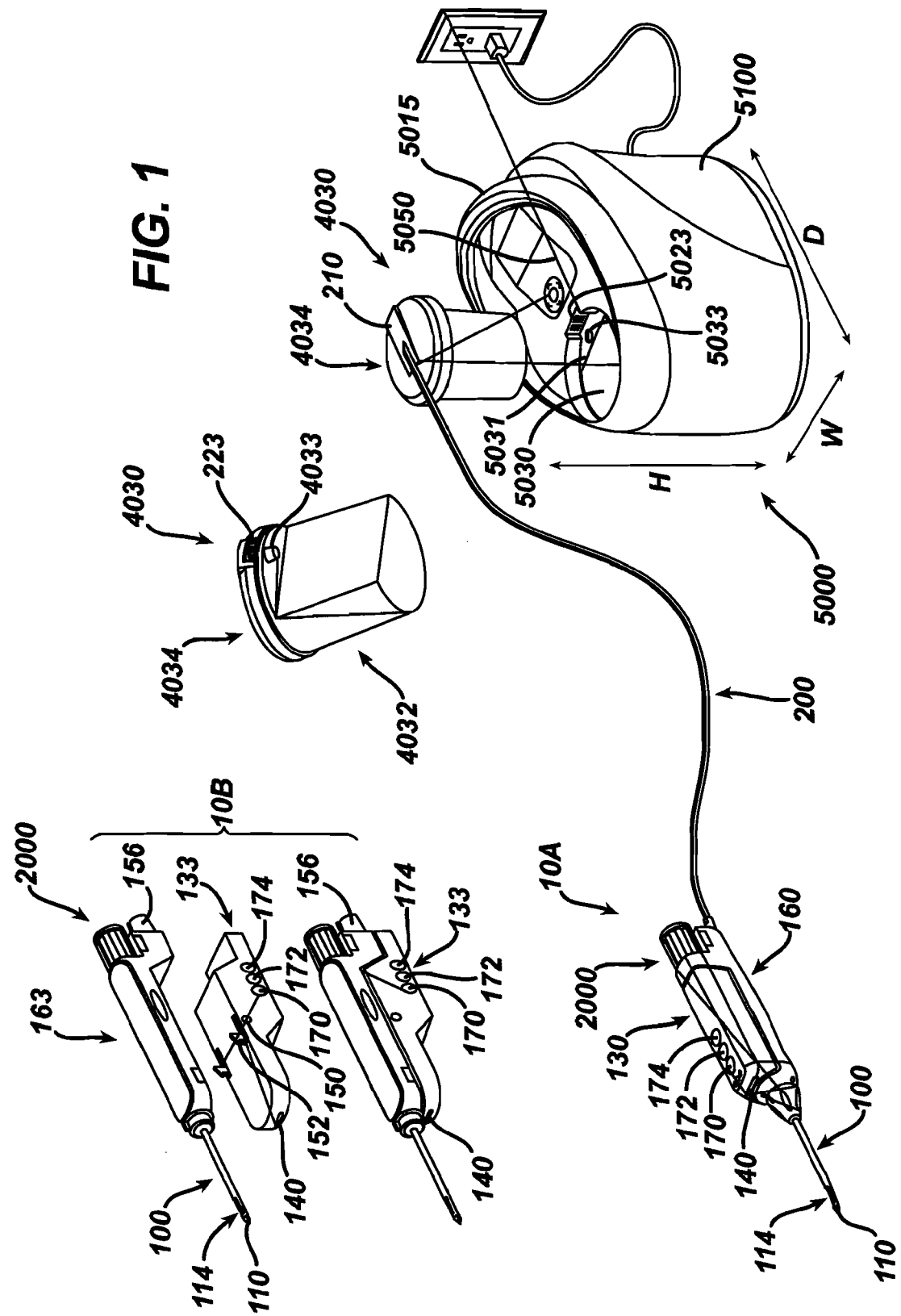
FIG. 1 is a schematic illustration of a biopsy system according to one embodiment of the present invention.

FIG. 1 illustrates a biopsy system according to one embodiment of the present invention. The biopsy system of the present example includes a biopsy device 10 having a translating cutter 120 for severing tissue samples, a vacuum control module 5000, and an umbilicus 200 extending from the biopsy device 10 to the control module 5000. The umbilicus 200 can be in the form of a cable having multiple lumens for providing one or more of electrical power, vacuum, pneumatics, hydraulics, or saline to the biopsy device 10. The biopsy device 10 can be a hand held device 10A such as is suitable for use with ultrasound imaging, or alternatively, a stereotactic device 10B configured to be mounted on a stereotactic or X-ray table. The vacuum control module 5000 can be a relatively lightweight, portable unit having a smoothly shaped outer cover 5100 and a carrying handle 5015. The lightweight control module 5000 of this example can be lifted and moved easily by a single person, with one hand. The multilumen umbilicus 200 of this example provides a single connection between the biopsy device 10 and the control module 5000, eliminating the complexity of having multiple electrical, saline, pneumatic, hydraulic, and/or vacuum lines extending from the biopsy device 10.

As noted above and as shown in FIG. 1, biopsy device 10 can be a handheld biopsy device 10A suitable for use with ultrasound imaging. The biopsy device 10A can include a reusable holster 130 and a disposable probe unit 160 that is detachable from holster 130. Together, the holster 130 and the probe 160 form a handpiece that can be comfortably held in and operated with a single hand. Biopsy device 10B can include a disposable probe unit 163, and a reusable stereotactic holster 133 having a firing mechanism for firing a tissue piercing portion of the biopsy device into tissue. The firing mechanism may be power driven (e.g., motorized), and may include a button 150 that may be actuated to activate the firing mechanism; as well as firing members 152 that are configured to engage probe 160 to fire at least a portion of probe 160 into tissue. Any suitable configuration for the firing mechanism may be used, to the extent that a firing mechanism is included at all. The stereotactic holster 133 can be configured for operable mounting onto a stereotactic X-ray table. Of course, biopsy device 10A and biopsy device 10B may alternatively be used in a variety of other settings or configurations.

Figure 1A:
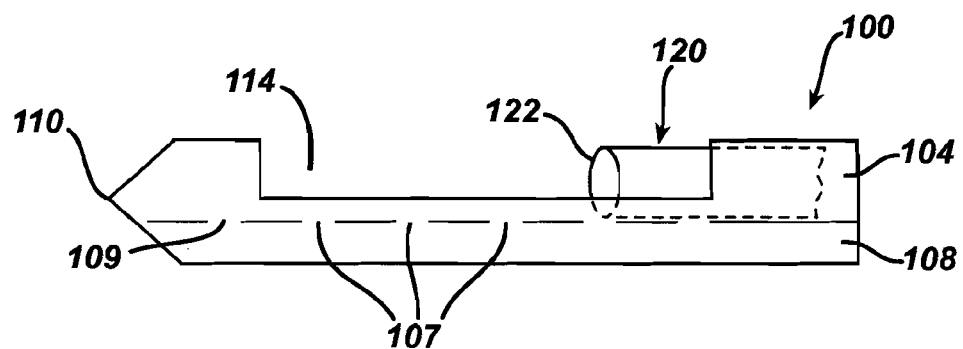
FIG. 1A is a schematic illustration of a distal portion of a tissue piercing cannula having a vacuum lumen and a cutter lumen, with the distal portion of the cutter shown in the cutter lumen.

The probe units 160 and 163 of the present example include a distally extending tissue piercing portion, such as a cannula 100 extending distally from probe 160. The cannula 100 can include a distal tissue piercing tip 110 and a tissue receiving aperture 114 spaced proximally of the tip 110. The cannula 100 can also include a cutter lumen 104 and a vacuum lumen 108, with passageways 107 and 109 providing flow communication between the lumen 104 and lumen 108 in the distal portion of cannula 100 (FIG. 1A). The cannula 100 can be inserted into or adjacent to a tissue mass to be sampled, and the biopsy device 10 is operable to obtain a plurality of severed tissue samples with a single insertion of cannula 100 into tissue.

Figure 1B:
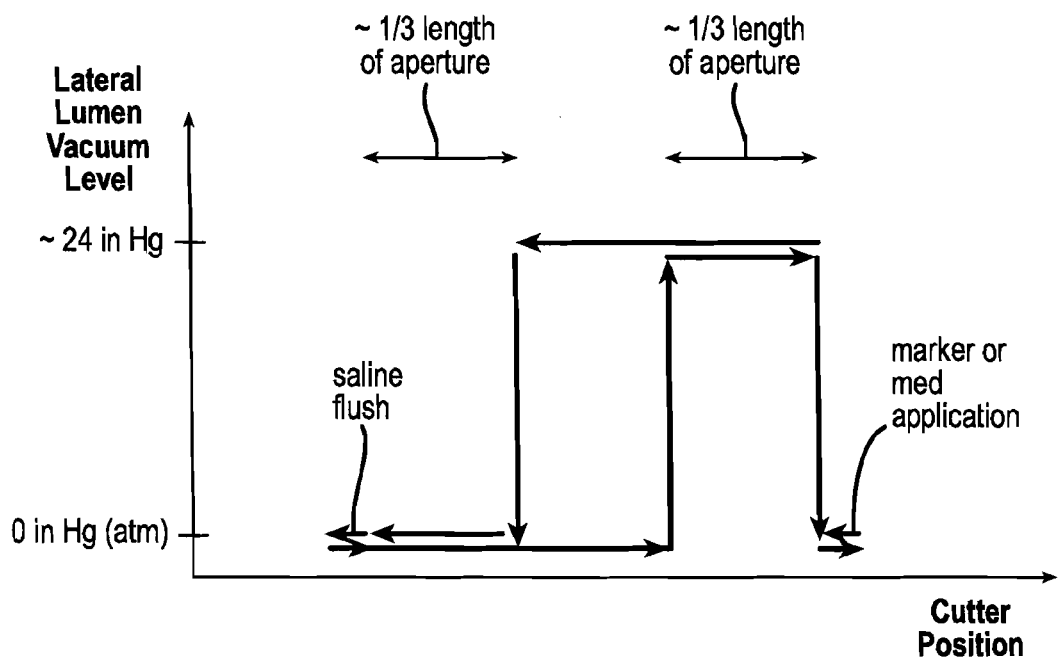
FIG. 1B is a schematic illustration of the vacuum level provided in a vacuum lumen as a cutter is advanced and retracted in a cutter lumen relative to a tissue receiving aperture.

With cannula 100 being inserted into tissue, tissue drawn into the aperture 114 can then be severed by sharpened distal end 122 (FIG. 1A) of a tubular cutter 120 translating within the cannula 100. Vacuum can be applied axially through the cutter 120 and also in vacuum lumen 108 to assist in drawing tissue into aperture 114. FIG. 1B illustrates graphically a variable vacuum level that can be provided in vacuum lumen 108 as the cutter 120 is translated relative to the aperture 114. The probe units 160 and 163 can also include a tissue storage assembly 2000, which can be disposed at a proximal end of the probe unit 160, 163 or elsewhere. The tissue storage assembly 2000 can be employed to store multiple tissue samples severed by the cutter translating within the cannula 100 and transferred proximally through the hollow cutter 120 to the tissue storage assembly 2000.

The probe units 160 and 163 of the present example each also include a light 140 positioned near cannula 100. By way of example only, light 140 may comprise an LED or other source of light, and may be configured to at least partially illuminate a site into which cannula 100 is to be inserted. Probe 163 also has a remote thumbwheel 156, which may be rotated to rotate the cannula 100 of probe 163 relative to the remainder of probe 163. Suitable mechanisms for causing such rotation will be apparent to those of ordinary skill in the art in view of the teachings herein. Of course, either probe 160, 163, as well as holsters 130, 133, may be subject to numerous variations and modifications as desired.

Vacuum control module 5000 of the present example can be portable by a single hand, and may have a weight of no more than about 40 pounds, and in one embodiment a weight of less than about 25 pounds. Alternatively, vacuum control module 5000 may be of any other suitable weight. The control module 5000 handle 5015 is shown extending upward from an upper portion of the unit, with the handle 5015 being the upper most component of the control module 5000, as shown in FIG. 1. The vacuum control module 5000 of the present example can have maximum outer dimensions of width W, depth D, and height H, each of which is less than about 1.5 feet. Alternatively, vacuum control module 5000 may have any other suitable dimensions. Vacuum control module 5000 of the present examples further includes a standard power cord for receiving electrical power from a standard electrical outlet.

Figure 2:
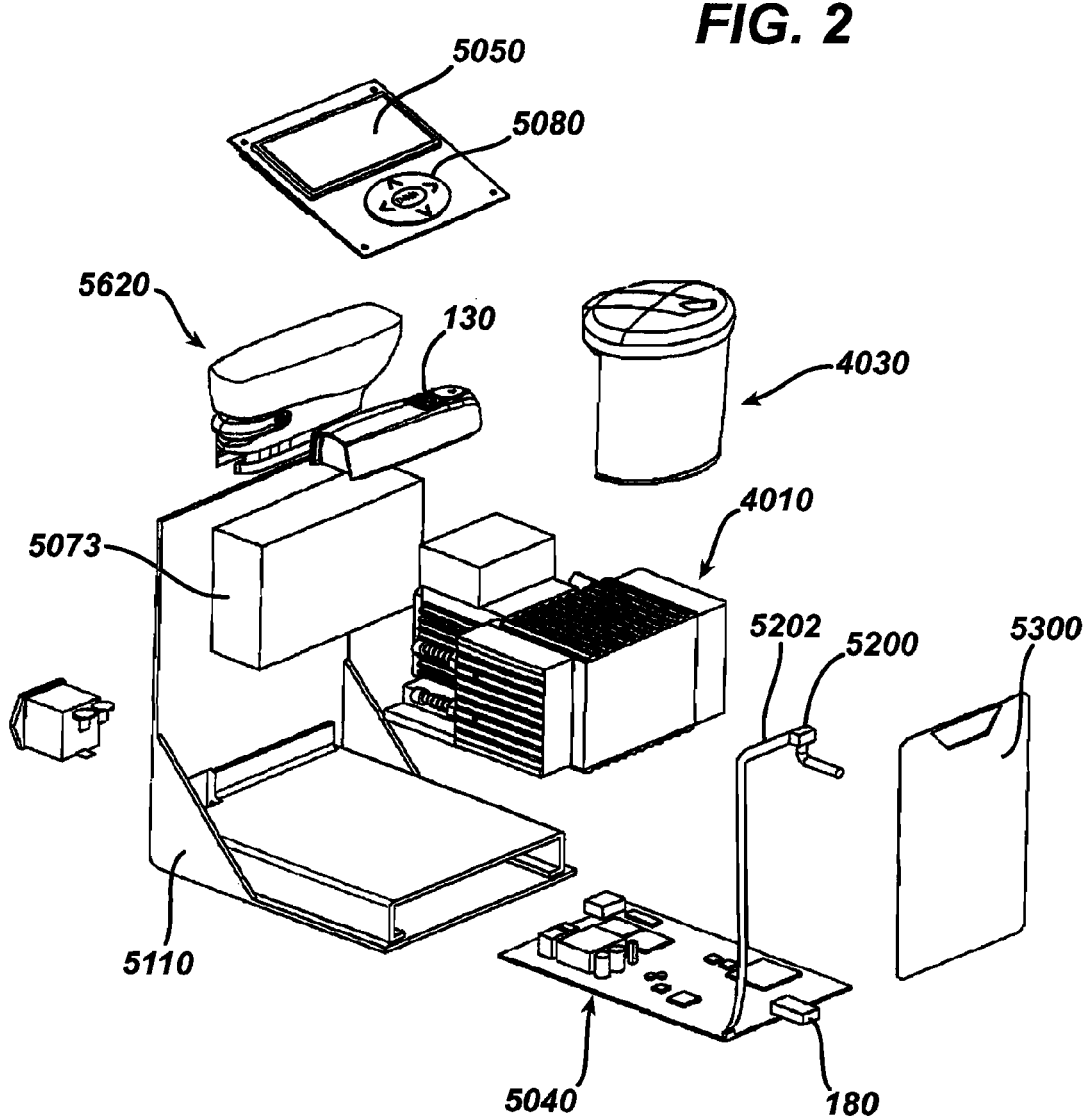
FIG. 2 is a schematic exploded view illustration of certain components of the vacuum control module depicted in FIG. 1.

FIG. 2 illustrates various components of the control module 5000 of the present example. The control module 5000 can include an internal aluminum (or other suitable metal) chassis 5110, which can directly or indirectly support a vacuum pump 4010, an AC/DC power supply 5073, and a microprocessor control board 5040. A suitable power supply 5073 may include a 250-Watt power supply model GPFC250 Commercial/GPFM250 Medical 250 manufactured by Condor D.C. Power Supplies of Oxnard, Calif. Alternatively, any other suitable power supply 5073 may be used. A suitable vacuum pump 4010 may include a 2-headed diaphragm pump having a maximum flow rate of less than about 18 liters per minute, and providing a maximum vacuum of about 25.1 inches of Mercury (Inch Hg.). Alternatively, vacuum pump 4010 may have any other suitable components and properties. By way of example only, one suitable vacuum pump 4010 may be a model 7006ZVDP-2.3E Diaphragm pump available from Reitschle Thomas, Thomas Products Division of Sheboygan, Wis.

The control module 5000 can also include an LCD display 5050, or other type of display, supported on an outside surface of the control module 5000, or elsewhere (e.g., external to control module 5000, etc.). By way of example only, display 5050 may include a backlit, color LCD display. Alternatively, any other type of display 5050 may be used, or no display 5050 at all. A keypad 5080 may also be provided, near display 5050, on control module 5000. Keypad 5080 may comprise capacitive switches or other input devices, and may be used to enter commands to or otherwise interact with control module 5000. Display 5050 may display operating conditions, menus, or other information, such that display 5050 and keypad 5080 collectively provide a user interface. Of course, a user interface may alternatively be provided using any other suitable components in any other suitable fashion.

In the present example, control module also has an attachment assembly 5200 that is configured to receive an off-the-shelf saline bag 5300. Attachment assembly 5200 is coupled with a flex circuit 5202, and is configured to sense the weight of a saline bag 5300. In particular, control module 5000 may be configured such that it will prevent operation of biopsy device 10 when no weight or insufficient weight is sensed by attachment assembly 5200, which may indicate that no saline bag 5300 is present or that the saline bag 5300 contains an insufficient amount of saline. In addition or in the alternative, control module 5000 may be configured to inform the user, such as via display 5050, that the a saline bag 5300 is not coupled with attachment assembly 5200 or that the saline bag 5300 contains an insufficient amount of saline. Alternatively, data from attachment assembly 5200 may be used in any other suitable way, or attachment assembly 5200 may be omitted altogether.

The vacuum control module 5000 of the present example can have a vacuum canister 4030 that is releasably received within an opening 5030 disposed in a generally upward facing outer surface of the control unit 5000. The vacuum canister 4030 may serve as a vacuum "capacitor" for the biopsy vacuum circuit, and can have a volume of less than about 300 cubic centimeters. More particularly, the vacuum canister 4030 can have a volume of about 200 to about 250 cc. Alternatively, vacuum canister 4030 may have any other suitable capacity or properties.

Figure 3:
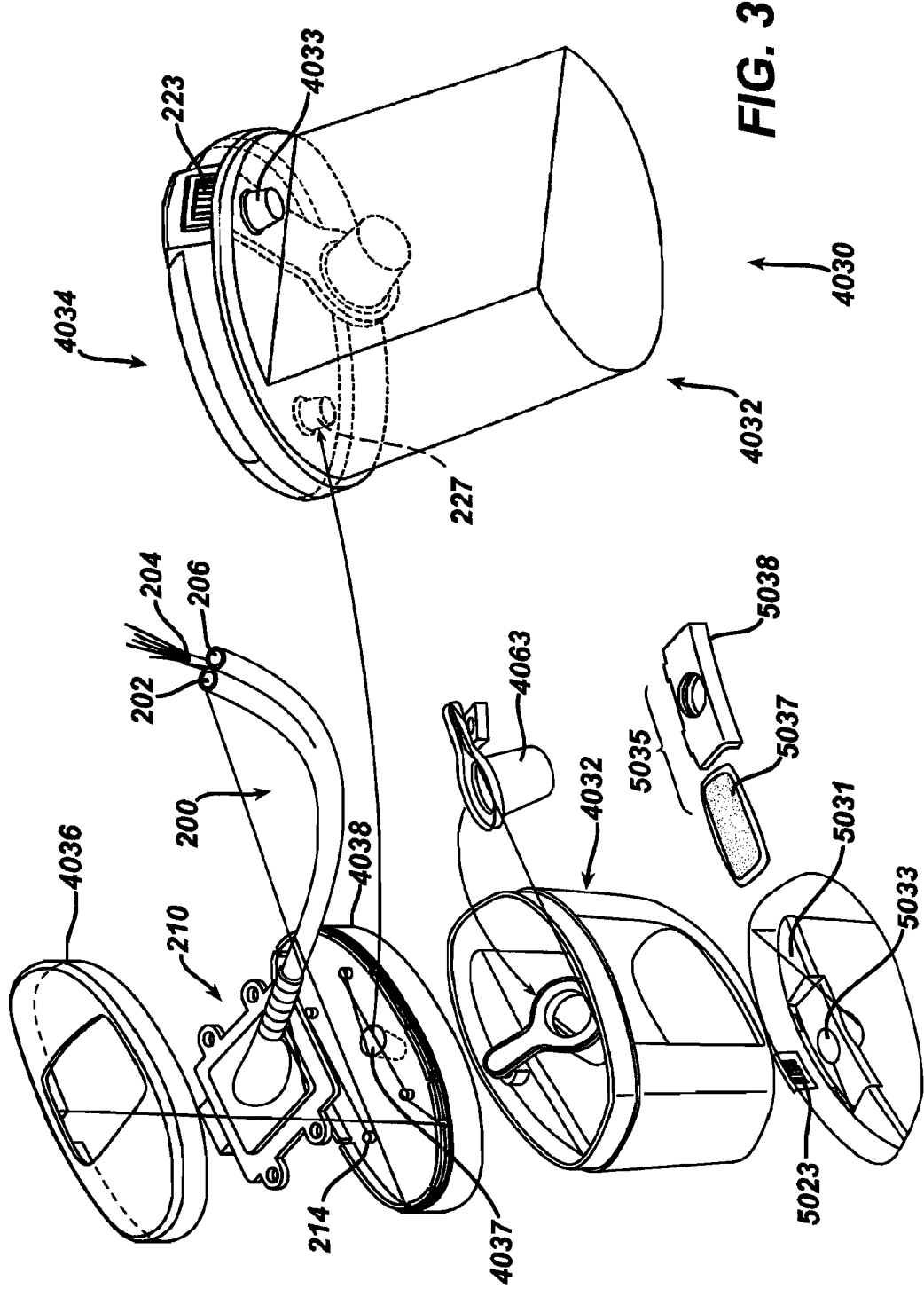
FIG. 3 is a schematic illustration of a vacuum canister that can be used with the biopsy system of FIG. 1.

Referring to FIG. 3, the umbilicus 200 of the present example can comprise multiple lumens, and can comprise a first lumen 202 for conveying vacuum from the vacuum pump 4010 to the biopsy device 10, a second lumen 204 for conveying one or more electrical conductors for conveying power and control signals from the control module 5000 to the biopsy device 10, and a third lumen 206 for conveying saline. Alternatively, umbilicus 200 may have any other suitable number or type of lumens. As yet another variation, one or more lumens 202, 204, 206 are provided in separate conduits or cables, instead of being integrated into a single umbilicus 200. The proximal end of the umbilicus 200 can include a connection terminator 210. The distal end of the umbilicus 200 can be received in the disposable portion of the biopsy device 10, such as the probe 160 or the probe 163, so that electrical power and control signals are directed through the disposable probe 160, and then to holster 130. One or more controls (e.g., control buttons 170, 172, 174, etc.) can be located on the reusable holster 130. Alternatively, the distal end of the umbilicus 200, or a portion thereof, may be received in holster 130 or elsewhere. Similarly, controls may be located on probe 160, 163 in addition to or in lieu of controls on holster 130.

The vacuum canister 4030 of the present example can include a cup or container shaped body portion 4032 and a lid 4034. The vacuum canister 4030 is configured to be inserted into an opening 5030 in an upwardly facing outer surface of the control module 5000. The canister 4030 can be supported on a lip 5031 that extends at least partially around the opening 5030. Of course, there are a variety of alternative ways in which vacuum canister 4030 may be configured; as well as alternative ways in which vacuum canister 4030 may engage with control module 5000.

In the present example, the body portion 4032 of the canister 4030 includes a male vacuum port 4033 communicating with the interior of the canister 4030. The port 4033 can sealingly engage a female vacuum port 5033 disposed in an opening in the lip 5031, when the canister 4030 is inserted into the opening 5030. In other variations, the lip 5031 or other portion of the control module 5000 may include a male vacuum port 4033; with the canister 4030 having a complimentary female vacuum port 5033. In the present example, the vacuum port 5033 can be connected with a flexible hose or tube or other conduit that communicates with the outlet of the vacuum pump 4010 disposed within the control module 5000. Accordingly, when the canister 4030 is inserted into the opening 5030 in the present example, a vacuum connection is established from the vacuum pump 4010 to the interior of the canister 4030.

The lid 4034 of the present example is adapted to receive the connection terminator 210 disposed at the proximal end of the umbilicus 200. The lid 4034 can include a upper, first lid portion 4036 and a lower, second lid portion 4038. The connection terminator 210 can be captured between the first and second lid portions 4036, 4038, and the two lid portions 4036, 4038 joined together (such as by a snap fit, by adhesive, or by any other suitable means). The position of the terminator 210 between the lid portions 4036, 4038 can be established by guide pins 212 on the lower lid portion which mate with corresponding guide holes 214 disposed around the perimeter of the terminator 210. Alternatively, any other suitable structures or features may be used to establish the position of the terminator 210 between the lid portions 4036, 4038, if any are used at all. Indeed, lid 4034 may instead be formed of a single piece instead of two lid portions 4036, 4038, and umbilicus 200 may be secured relative thereto in any other suitable fashion. The multilumen umbilicus 200 and the vacuum canister 4030 can be provided as separate disposable items or provided together as a unitary disposable item.

Figure 4:
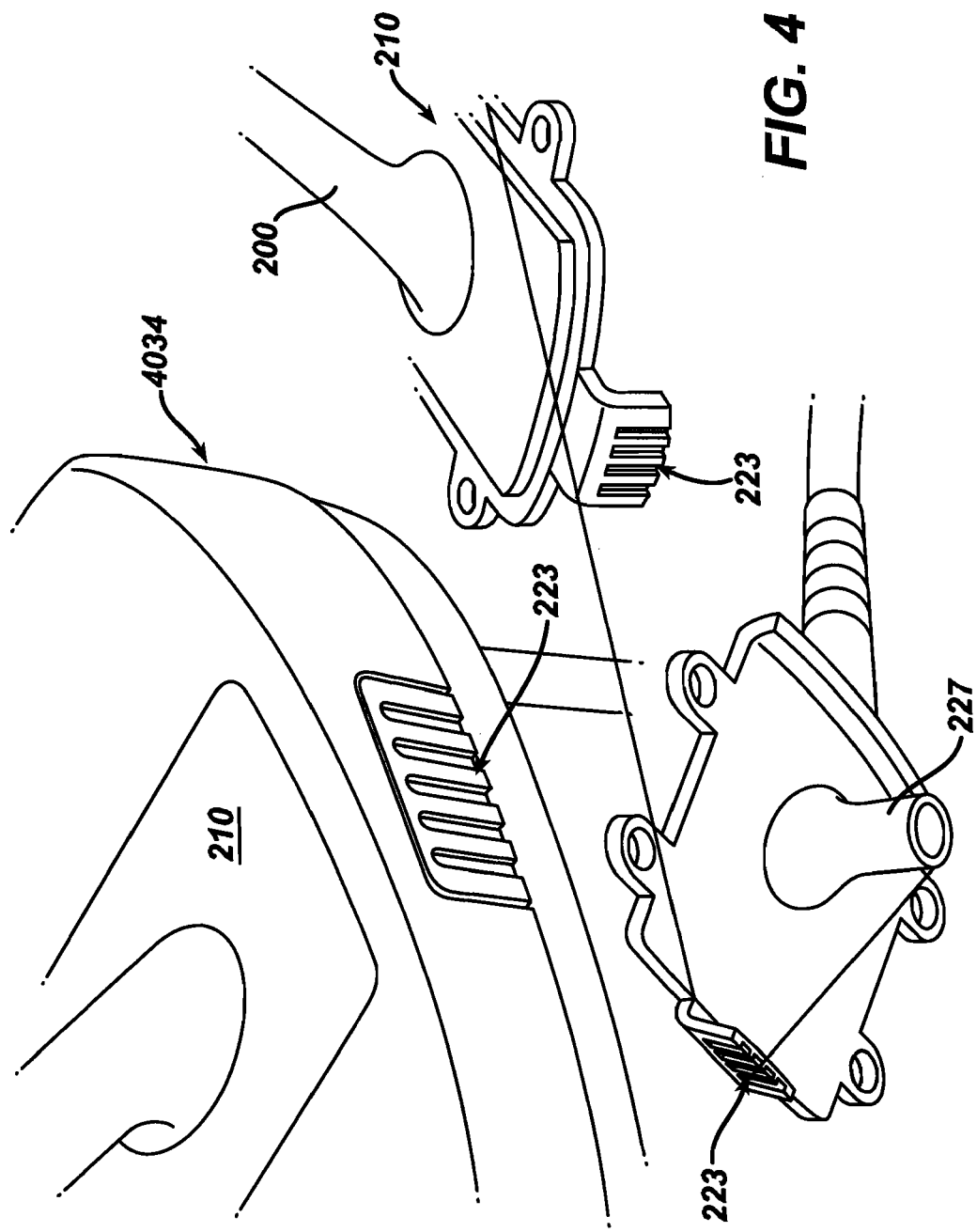
FIG. 4 is a schematic illustration of the interface of a multilumen cable and a vacuum canister cover.

As shown in FIGS. 1, 3, and 4, the connection terminator 210 of the present example provides a multi-contact electrical connection 223, which faces outward from the lid 4034 when the terminator 210 is positioned on the lid 4034. The control module 5000 includes a mating multi-contact electrical connection 5023. The multi-contact connection 5023 is disposed adjacent the opening 5030 of the control module 5000, such that when the vacuum canister 4030 is positioned in the opening 5030, the electric contact is established between the control module 5000 and the multilumen umbilicus 200 via the contacts 223 and 5023. It will be appreciated, however, that electrical contact may be provided between control module 5000 and umbilicus 200 using a variety of alternative structures and techniques.

Referring to FIGS. 3 and 4, the connection terminator 210 can further include a downward facing male vacuum port 227 extending from a bottom surface of the connection terminator 210. The vacuum port 227 communicates with the vacuum lumen 202 in umbilicus 200. When terminator 210 is disposed on lid 4034 between lid portions 4036 and 4038, the vacuum port 227 extends through an opening 4037 in the lower lid portion 4038 to communicate with the interior of the vacuum canister 4030. Alternatively, vacuum lumen 202 may communicate with the interior of the vacuum canister 4030 using any other suitable structures or techniques.

Accordingly, in the present example, the vacuum canister 4030, terminator 210, and control module 5000 are configured such that positioning the canister 4030 in the opening 5030 of the control module 5000 provides an electrical connection and vacuum communication between the biopsy device 10 and the vacuum control module 5000. In other words, fluid and electrical connections between biopsy device 10 and the vacuum control module 5000 are established merely by inserting the canister 4030 into opening 5030, such that additional tube connections or cable connections (e.g., connection of a tube with the canister 4030), etc. need not be established by the user before or after canister 4030 is inserted into opening 5030. As used herein, the term "fluid" should be read to include a vacuum, pressurized air, atmospheric air, liquids (e.g., saline, blood, etc.), and the like, regardless of whether solid materials (e.g., tissue samples or particles, etc.) are conveyed therewith.

Still referring to FIGS. 3 and 4, a float 4063 can be positioned in the canister 4030. The float 4063 is operable to close vacuum port 4033 in the event fluid accumulates in the canister above an acceptable level. A filter assembly 5035 including a filter pad 5037 and filter pad cover 5038 can be provided at the vacuum port 5033 if desired. Of course, like other components described herein, float 4063, filter assembly 5035, filter pad 5037, and filter pad cover 5038 are all merely optional, and may be modified, substituted, supplemented, or omitted as desired.

Figure 5:
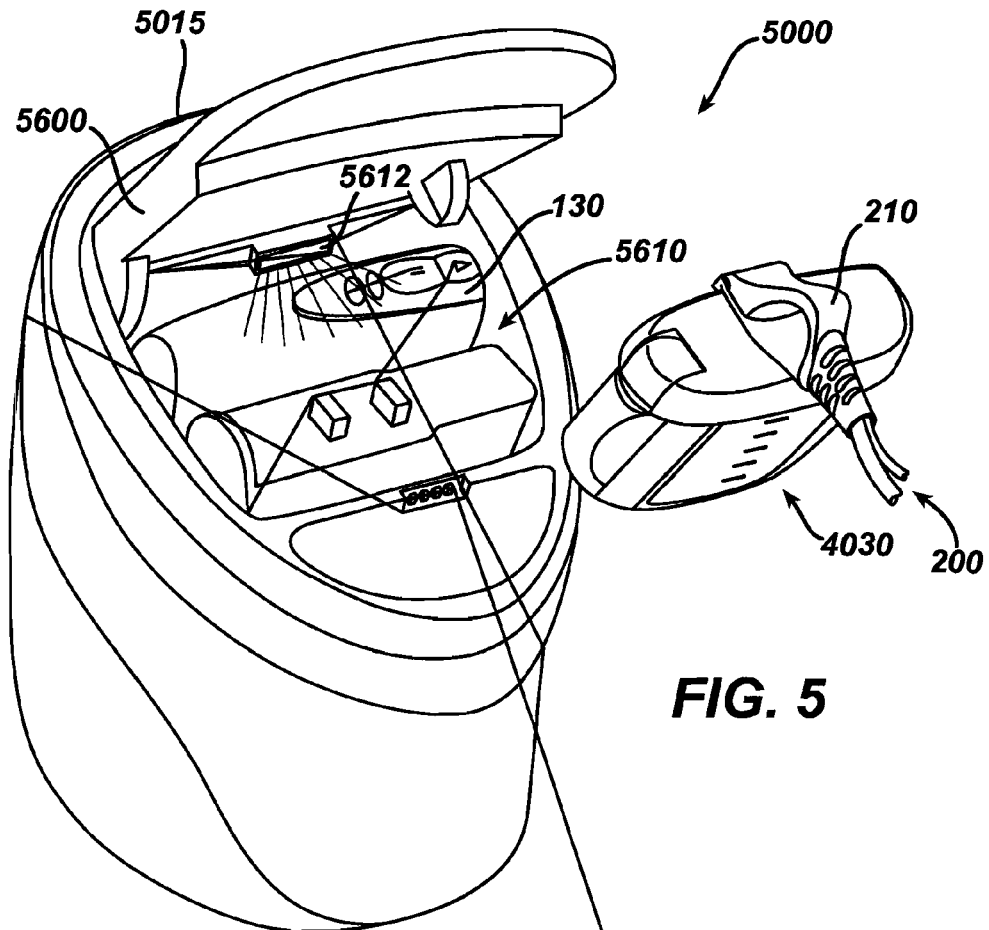
FIG. 5 is a schematic illustration of a control module including a handle and a hinged lid.

FIG. 5 provides a schematic illustration of an embodiment of the control module 5000 that includes a hinged cover 5600. Cover 5600 covers a storage cavity 5610, similar to tissue storage compartment 5620 of the control module shown in FIG. 2. The storage cavity 5610 can be sized to store one or more biopsy device holsters 130. If desired, a plurality of UV light sources 5612 (only one shown) can be positioned near or within cavity 5610. Light sources 5612 can be configured to be "on" when the cover 5600 is closed (and "off" when the cover 5600 is opened), and can be employed to disinfect or sterilize the item(s) stored in the cavity 5610. In other embodiments, other components, features, or devices are included to disinfect or sterilize one or more items stored in the cavity 5610, in addition to or in lieu of having light sources 5612. In still other embodiments, no features are included for disinfecting or sterilizing items. Similarly, some variations of control module 5000 lack a cavity 5610 altogether.

Figure 5A:
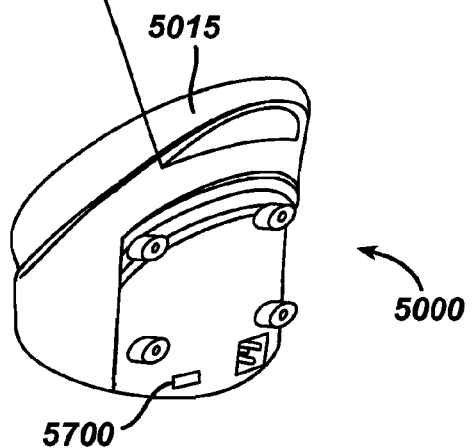
FIG. 5A illustrates a USB port positioned on the back surface of the control module of FIG. 5.
Figure 6:
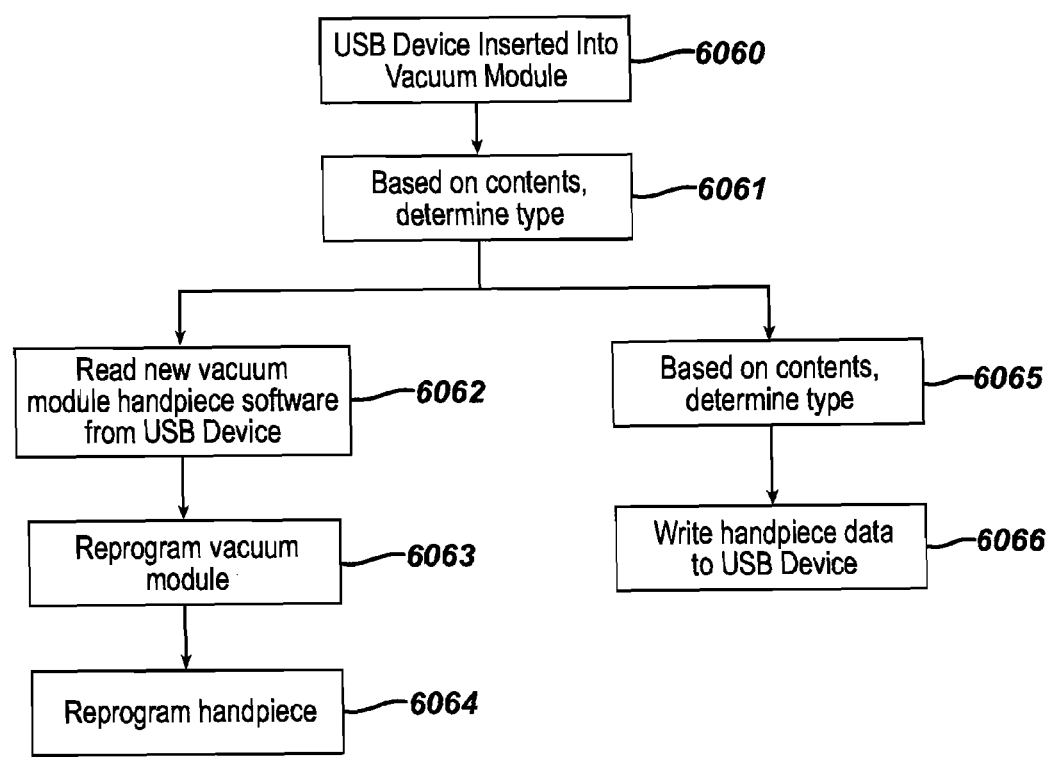
FIG. 6 illustrates various steps that can be performed with respect to a USB device inserted into a USB port on a control module.

Referring to FIG. 5A, one or more Universal Serial Bus (USB) ports 5700 can be provided on an outer surface of the control module 5000. Alternatively, any other type of port (e.g., an SD card slot, an ethernet port, a serial connection port, a proprietary connection port, etc.) may be provided on control module 5000. FIG. 6 illustrates a flow chart describing a sequence of operational steps that can be employed when a USB memory device (not shown) is coupled with control module 5000 via port 5700. Based on the contents of the USB memory device, a course of action can be determined. For instance, based on the contents of the USB memory device, the control module microprocessor control may write vacuum control module data to the USB memory device (e.g., usage time, operational status, first use or first in service date, and the like.) The control microprocessor control may also write biopsy device data to the USB memory device (e.g., usage time, operational status, first use, or first in service date). Alternatively, the vacuum control module 5000 may read new calibration information, software, or software updates, etc., from the USB memory device, reprogram operation of the vacuum module, and/or reprogram operation of the biopsy device 10. Alternatively, a computer (e.g., desktop or laptop PC), or network (e.g., internet) connection may be made with control module 5000 via port 5700 or in some other fashion.

Figure 7:
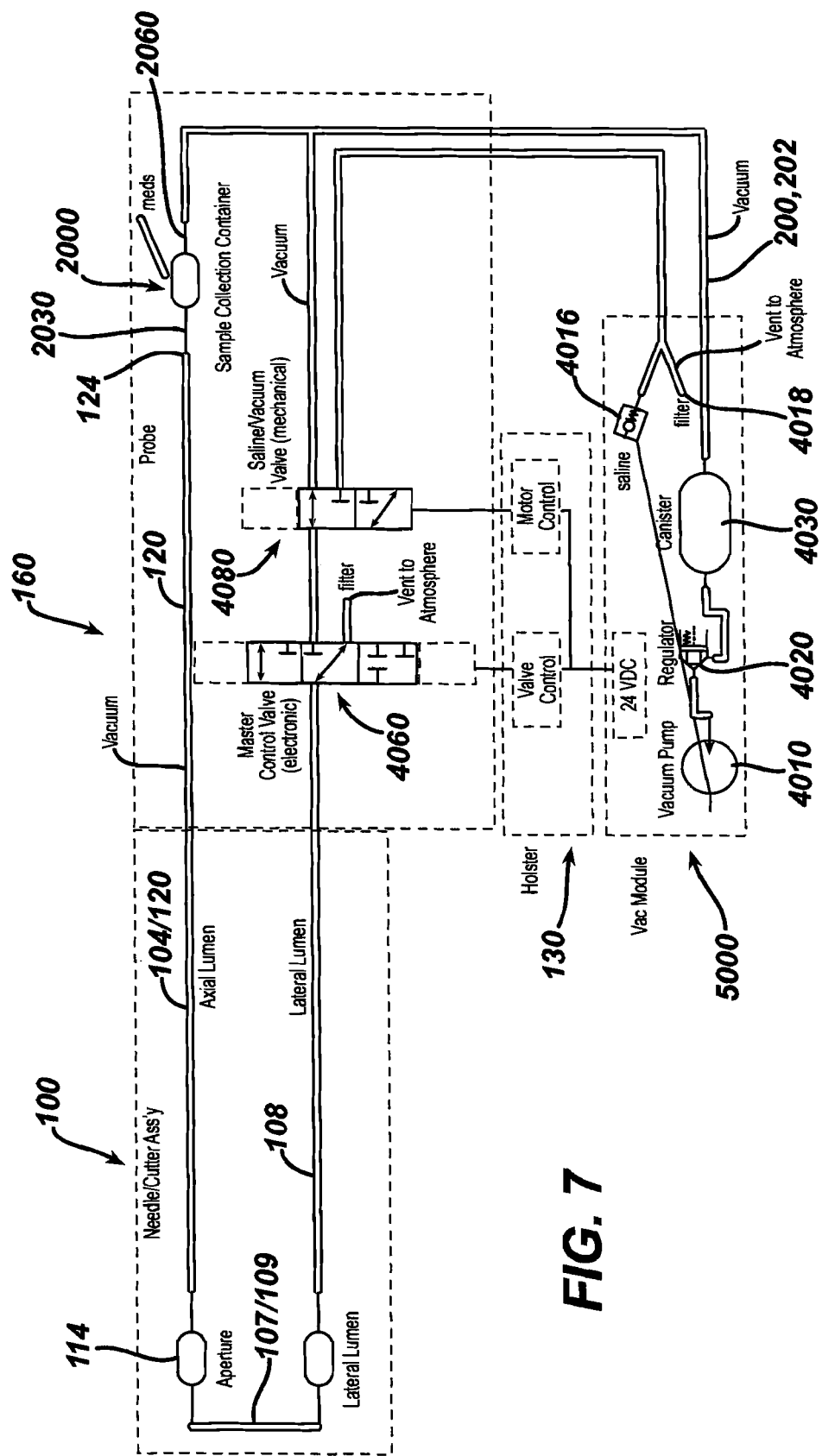
FIG. 7 illustrates a pneumatic circuit that may be used with a biopsy system.

FIG. 7 is a schematic illustration of a pneumatic configuration that can be used with the biopsy device 10 and vacuum control module 5000 of the present example. FIG. 8 illustrates multiple control states that can be employed in controlling the biopsy device 10.

As shown in FIG. 7, the control module 5000 of the present example comprises the vacuum pump 4010, a regulator 4020, and a the vacuum canister 4030 disposed in a pneumatic circuit. A master control valve 4060 and a saline/vacuum valve 4080 are shown schematically as being positioned in the disposable probe 160.

The vacuum provided by vacuum pump 4010 can be directed through the vacuum lumen 202 of umbilicus 200 to the disposable probe 160, to provide vacuum to the cutter 120 and cutter lumen 104. This vacuum can be provided without valving, so that the vacuum provided to the interior of cutter 120 and to cutter lumen 104 of cannula 100 is always "on" when vacuum pump 4010 is operating. Alternatively, one or more valves or similar components may be provided in probe 160, canister 4030, control module 5000, and/or elsewhere. The vacuum provided by umbilicus 200 can also provide a vacuum to the vacuum lumen 108 via the two valves 4060 and 4080. Valve 4080 can be a 3-port/2-position valve, with two input ports. One input port can be connected to the vacuum source and the other input port can be connect to a source of saline 4016 (or alternatively vented to atmospheric pressure through filter 4018). The output port of valve 4080 communicates with an import port of master valve 4060. Other suitable configurations and couplings for the ports will be apparent to those of ordinary skill in the art in view of the teachings herein.

The operational position of the valve 4080 can be configured to correspond to the position of the cutter 120, such as by having cutter 120 extend through the valve 4080 so that the position of the cutter 120 within the valve body determines the operational status (opened or closed) of the valve ports. When the cutter 120 is retracted proximally (e.g., such that tissue aperture 114 is open), the valve 4080 communicates vacuum to the master control valve 4060. When the cutter 120 is advanced distally (e.g., such that tissue receiving aperture 114 is closed), the valve 4080 communicates saline to the master control valve 4060. Alternatively, if saline is not available, or not desired, then valve 4080 communicates atmospheric air via filter 4018 to the master control valve 4060. The valve 4060 can be actuated by a microprocessor controlled motor, by a mechanical link to the cutter 120, or otherwise. The valve 4080 can be spring loaded in one position, and movement of the cutter 120 (such as movement of the cutter 120 to the distal position) can be employed to change the valve operational position. Alternatively, the operational position of the valve 4080 can be configured to correspond to the position of the cutter 120 in any other suitable way. Furthermore, valve 4080 may be configured such that its operational position does not necessarily correspond with the position of the cutter 120.

The master control valve 4060 can be a 3-port/3-position valve. One input port can be connected to the output port of the valve 4080. The second input port can be vented to filtered atmospheric air. The output port of the valve 4060 can be connected to the proximal end of vacuum lumen 108 of cannula 100. The valve position of valve 4060 can be controlled by the operator of the biopsy device 10 using one or more user control interfaces, such as the control buttons 170, 172, 174 listed in FIG. 8 or any other interface. The control buttons 170, 172, 174 can be located at any convenient position on the body of the biopsy device 10, including for instance on handpiece 130, or elsewhere. The valve 4060 can be actuated by a solenoid, motor, via a link to the cutter 120, or otherwise.

With reference to FIG. 8, the "Ready State" of biopsy device 10 corresponds to the cutter 120 being advanced to its distal most position and tissue aperture 114 being closed. In the Ready State, the valve 4080 communicates saline to the master control valve 4060 and the master control valve is positioned to seal off (close) its other ports, including the output port communicating with vacuum lumen 108. By closing the port to the lateral lumen 108 while in the Ready State, airflow through the device may be minimized, which may allow the pump 4010 to more easily maintain the desired vacuum level at the vacuum canister 4030.

When the operator depresses the "Sample" button 170 in the present example, the cutter motor is activated to cause the cutter 120 to retract proximally. As the cutter retracts, the valve 4080 changes position to communicate vacuum to the master control valve 4060. At the same time, the master control valve changes position to communicate a vacuum to the vacuum lumen 108. With the tissue aperture 114 open, vacuum from vacuum pump 4010 is applied to the cutter 120 (such as via the tissue storage assembly 2000) and cutter lumen 104 (via the cutter 120), as well as to the vacuum lumen 108 (via the valves 4080 and 4060). Vacuum applied to both cutter lumen 104 and vacuum lumen 108 assists in prolapsing tissue into aperture 114 of cannula 100.

After maintaining this vacuum state for a second or more to ensure tissue has prolapsed into aperture 114, the cutter 120 is advanced distally (and simultaneously rotated) to close the aperture 114 and severe a tissue sample in the distal portion of the hollow cutter 120. As the cutter 120 advances distally, the cutter 120 can contact or otherwise actuate the valve 4080 to change the valve position to communicate saline to the master control valve 4060. Also, as the cutter 120 advances, a microprocessor can be employed to change the master control valve 4060 position to communicate filtered atmospheric air to vacuum lumen 108, which in turn is communicated via passageways 107, 109 to the distal face of the severed tissue sample positioned in the distal portion of hollow cutter 120. The atmospheric air on the distal face of the tissue sample provides a proximal pushing force on the tissue sample, while the vacuum provided in cutter 120 (via the tissue storage assembly 2000) provides a proximally directed pulling force on the severed tissue sample. The resulting proximally directed force on the tissue sample conveys the tissue sample through the hollow cutter 120 into tissue storage assembly 2000. Of course, any other suitable structures or techniques may be used to capture a tissue sample and communicate it to a tissue storage assembly 2000.

In an alternative embodiment, the microprocessor can be employed to change the position of master control valve 4060 to first communicate saline to vacuum lumen 108 for a predetermined period of time, and then change the valve's position to communicate atmospheric air to the lumen 108.

Accordingly, a fixed volume of saline can be delivered via passageways 107, 109 to the distal end of hollow cutter 120, thereby assisting in moving the severed tissue sample proximally through hollow cutter 120 to tissue storage assembly 2000. The control system can be programmed to return to the Ready State after a predetermined period of time (e.g., one or more seconds).

The biopsy device operator can depress the "Clear Probe" button 172 while in the Ready State (e.g., after having operated the "Sample" button 170 to sever tissue) in order to direct a microprocessor control to cause the cutter 120 to reciprocate slightly to open and close aperture 114 a fraction of an inch (e.g. 0.2 inches), or to any suitable degree. This reciprocation of cutter 120 can be effective to dislodge the tissue sample or otherwise free the sample so that the sample can travel freely through hollow cutter 120. While the cutter 120 is reciprocating, the vacuum control valve 4060 can be repositioned to communicate saline to the vacuum lumen 108 and through passageways 107, 109 to provide a pushing force on the distal face of the tissue sample. After a predetermined period of time, the microprocessor can return the pneumatic system to the Ready State.

The operator can depress and release the "Aspirate/Insert" button 174 when the device is in the Ready State to insert medication or a tissue marker into the tissue being sampled or into the site from which a tissue sample has been or will be taken. When the button 174 is depressed in this example, the cutter 120 moves proximally to open aperture 114. The position of the master control valve 4060 is changed to communicate atmospheric air to the vacuum lumen 108. Depressing the "Aspirate/Insert" button 174 also turns off the vacuum (such as by either turning off the pump 4010 or opening regulator 4020 to vent pump 4010 outlet to atmosphere, etc.). The tissue marker applier (or medication) can be fed into the proximal end of the cannula 100 through hollow cutter 120, such as via the tissue storage assembly 2000 or otherwise, with the marker (or medication) being then deployed through the open aperture 114 in cannula 100. After the marker or medication has been deployed, the user may press any button, which may advance the cutter 120 to return to the Ready State with the master control valve 4060 positioned up.

The operator can depress and hold the "Aspirate/Insert" button 174 to aspirate fluid in the vicinity of aperture 114. When the operator depresses the button 174 in this example, the cutter 120 moves proximally to open aperture 114. With the cutter positioned proximally, the valve 4080 communicates vacuum to the master control valve 4060, and the master control valve 4060 is positioned to communicate vacuum to the vacuum lumen 108. Accordingly, vacuum is applied to both the lumen 108 and the cutter lumen 104 (because vacuum is provided continuously through cutter 120 to lumen 104 while the pump 4010 operates in this example). The vacuum provided to lumen 104 and lumen 108 aspirates any liquid near the aperture 114. When the Aspirate/Insert button 174 is released, the pneumatic system is controlled to return the Ready State. The cutter 120 is advanced to close aperture 114. As the cutter 120 is advanced in this example, the master control valve 4060 is positioned to communicate filtered atmospheric air to the vacuum lumen 108. Once the aperture 114 is closed, the master control valve 4060 is positioned to close all its ports to attain the Ready State. As with other operational sequences described herein, the foregoing operational sequence is merely illustrative, and any other suitable operational sequences may be used in addition to or in lieu of those explicitly described herein.

The length of the umbilicus 200 from the control module 5000 housing the vacuum pump 4010 to the biopsy device 10 can be relatively long (as much as 20 feet or more in some cases) in order to accommodate movement of the biopsy device 10 in the operating room, or due to limitations of the position of the control module 5000 in magnetic resonance imaging environments. Of course, umbilicus 200 may be of any desired length. In the present example, the vacuum line in the umbilicus 200 can account for a considerable portion of the flow volume that needs to be supplied or maintained by the vacuum pump 4010 and vacuum canister 4030 when the tissue aperture 114 is open. Placing the saline vacuum valve 4080 and the master control valve 4080 at the distal end of the vacuum line (the end associated with the biopsy device 10) instead of in the biopsy vacuum control unit 5000 may mean that a smaller vacuum pump 4010 and a smaller vacuum canister 4030 can be used. In some conventional biopsy devices, valving may be placed in the control unit that includes the vacuum pump, and the control unit is may be mounted on wheels due to its weight and size. In FIGS. 2-4, the valves 4060 and 4080 are shown disposed in the biopsy device 10. The valves can be disposed in a disposable probe portion 160, 163 that includes the cannula 100 and cutter 120 and/or in a non-disposable (e.g., in the holster 130) portion of the biopsy device 10. Such a valve placement may allow a relatively low weight diaphragm vacuum pump 4010 having a flow rate of about 18 liters per minute to be used, as compared to a conventional pump and valve arrangement requiring more than 80 liters per minute. Of course, any desired vacuum pump having any desired properties may be used.

Similarly, the vacuum canister 4030 can be relatively small, with a volume of less than about 300 cubic centimeters, as compared to a conventional vacuum canister having a volume storage capacity of 1200 cc's or more. As a result, a relatively lightweight, hand-portable vacuum control module 5000 can be employed. The vacuum control module 5000 (FIGS. 1, 2, and 5) can weigh less than 25 pounds, can be carried by one hand, and can have height, width, and length dimensions each less than about 1.5 feet. Alternatively, vacuum canister 4030 and control module 5000 may have any other suitable capacity, size, weight, or other properties.

If desired, a foot pedal (not shown) or remote keypad (not shown) can be employed to provide control input or instructions to the biopsy device 10 directly and/or to the vacuum control module 5000, such as via a connector 180. The foot pedal and remote keypad can be tethered (e.g., with one or more wires extending from the food pedal/keypad to the vacuum control module 5000, etc.). Alternatively, "wireless" communication between the foot pedal/keypad and the control module 5000 and/or the biopsy device 10 can be employed. For instance, wireless "Bluetooth" communication and associated hardware and software can be employed to provide wireless control signals to the vacuum control module 5000 and/or the biopsy device 10 without requiring a "line of sight" for signal transmission and reception. Alternatively, an infrared transmitter and receiver can be employed to send and receive control signals. Other ways in which communication may be provided between components of a biopsy system (e.g., between a pedal/keypad and control module 5000), whether wired, wireless, or otherwise, will be apparent to those of ordinary skill in the art in view of the teachings herein.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims.

Additionally, each element described in relation to the invention can be alternatively described as a means for performing that element's function.

What is claimed is:

1. A biopsy system comprising:
  a biopsy probe comprising:
    a cannula having a closed distal end, a tissue receiving port spaced proximally of the closed distal end, a first lumen, and a second lumen in fluid communication with the first lumen through a plurality of passageways, the cannula extending from the probe;
    a cutter having a cutter lumen, the cutter configured for translation relative to the tissue receiving port of the cannula for severing tissue;
    a tissue storage assembly positioned to receive tissue samples communicated proximally through the cutter lumen, wherein the cutter is configured to transport severed tissue samples proximally through the cutter lumen to reach the tissue storage assembly; and
    a first valve disposed on the probe, wherein at least a portion of the cutter extends through the first valve such that the position of the cutter within the valve determines an operational status of at least one port of the first valve, wherein a first operational status of the at least one port of the first valve is operable to vent the second lumen permitting a vacuum applied to the cutter lumen to urge a tissue sample proximally though the cutter lumen, wherein a second operational status of the at least one port of the first valve is operable to provide vacuum to the second lumen permitting prolapse of tissue into the tissue receiving port.

2. The biopsy system of claim 1 wherein the biopsy probe comprises a second valve separate from the first valve.

3. The biopsy system of claim 2 wherein an output port of the first valve communicates with an inlet port of the second valve.

4. The biopsy system of claim 1 wherein the position of the cutter within a valve body is operable to communicate a source of saline with a second valve.

5. The biopsy system of claim 2 wherein proximal retraction of the cutter operates the first valve to communicate vacuum to the second valve.

6. A handheld biopsy device comprising:
  a handpiece sized and shaped to be grasped and manipulated by a single hand and without aid of an external support;
  a cannula extending from a distal end of the handpiece, the cannula having a closed distal end, a first lumen, a second lumen, and a tissue receiving port spaced proximally of the closed distal end in fluid communication with the first lumen;
  a cutter having a cutter lumen, the cutter configured for translation relative to the tissue receiving port of the cannula for severing tissue;
  a first valve having a valve housing disposed in the handpiece, wherein the first valve is operable to vent the second lumen to permit the transport of a tissue sample proximally through the cutter lumen by a vacuum applied to the cutter lumen, wherein the first valve is further operable to apply vacuum to the second lumen to prolapse tissue into the tissue receiving port; and
  a tissue storage assembly located at the proximal end of the handpiece;
  wherein at least a portion of the cutter extends through the first valve housing; and
  wherein the cutter is movable within the first valve housing.

7. The device of claim 6 wherein the handpiece is configured to communicate vacuum to the cutter via the tissue storage assembly.

* * * * *